(12) United States Patent
Shah et al.

(10) Patent No.: US 8,137,927 B2
(45) Date of Patent: Mar. 20, 2012

(54) MOLDED PROTEIN MATERIAL IN FORM OF PELLET FOR SENSOR

(75) Inventors: Rajiv Shah, Rancho Palos Verdes, CA (US); Bahar Reghabi, Los Angeles, CA (US); Rudy Montalvo, Woodland Hills, CA (US); Yanan Zhang, Valencia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1032 days.

(21) Appl. No.: 11/122,172

(22) Filed: May 4, 2005

(65) Prior Publication Data

US 2005/0214741 A1 Sep. 29, 2005

Related U.S. Application Data

(62) Division of application No. 10/033,723, filed on Dec. 27, 2001, now Pat. No. 7,192,766.

(60) Provisional application No. 60/335,663, filed on Oct. 23, 2001.

(51) Int. Cl.
*C12Q 1/26* (2006.01)
*C12Q 1/54* (2006.01)
*C12N 11/02* (2006.01)
*C12M 1/34* (2006.01)

(52) U.S. Cl. ......... 435/25; 435/14; 435/177; 435/287.1; 435/817

(58) Field of Classification Search .................. None
See application file for complete search history.

(56) References Cited

U.S. PATENT DOCUMENTS

| | | | |
|---|---|---|---|
| 4,240,438 A | 12/1980 | Updike et al. | |
| 4,478,946 A | 10/1984 | Van der Merwe et al. | |
| 4,479,796 A | 10/1984 | Kallok | |
| 4,484,987 A | 11/1984 | Gough | |
| 4,486,408 A | 12/1984 | Kiel et al. | |
| 4,568,335 A | 2/1986 | Updike et al. | |
| 4,628,928 A | 12/1986 | Lowell | |
| 4,650,547 A | 3/1987 | Gough | |
| 4,703,756 A | 11/1987 | Gough et al. | |
| 4,757,022 A | 7/1988 | Shults et al. | |
| 4,771,772 A | 9/1988 | DeWitt | |
| 4,876,324 A | 10/1989 | Nakano et al. | |
| 4,879,072 A * | 11/1989 | Bourset et al. ............... | 264/1.36 |
| 4,890,620 A | 1/1990 | Gough | |
| 4,891,104 A * | 1/1990 | Liston et al. ............. | 204/403.05 |
| 4,911,168 A | 3/1990 | Davis | |
| 4,970,156 A | 11/1990 | Avrameas et al. | |
| 4,994,167 A | 2/1991 | Shults et al. | |
| 5,094,951 A | 3/1992 | Rosenberg | |
| 5,266,688 A | 11/1993 | Rosenberg | |
| 5,270,446 A | 12/1993 | Kyogoku et al. | |
| 5,328,460 A | 7/1994 | Lord et al. | |
| 5,497,772 A | 3/1996 | Schulman et al. | |
| 5,534,025 A | 7/1996 | Moussy | |
| 5,593,852 A | 1/1997 | Heller et al. | |
| 5,660,163 A | 8/1997 | Schulman et al. | |
| 5,667,983 A | 9/1997 | Abel et al. | |
| 5,696,314 A | 12/1997 | McCaffrey et al. | |
| 5,707,502 A | 1/1998 | McCaffrey et al. | |
| 5,711,868 A | 1/1998 | Maley et al. | |
| 5,728,281 A | 3/1998 | Holmstrom et al. | |
| 5,741,211 A | 4/1998 | Renirie et al. | |
| 5,741,319 A | 4/1998 | Woloszko et al. | |
| 5,770,028 A | 6/1998 | Maley et al. | |
| 5,773,270 A | 6/1998 | D'Orazio et al. | |
| 5,791,344 A | 8/1998 | Schulman et al. | |
| 5,795,774 A | 8/1998 | Matsumoto et al. | |
| 5,804,048 A | 9/1998 | Wong et al. | |
| 5,919,216 A | 7/1999 | Houben et al. | |
| 5,932,175 A | 8/1999 | Knute et al. | |
| 5,941,906 A | 8/1999 | Barreras, Sr. et al. | |
| 5,964,993 A * | 10/1999 | Blubaugh et al. ........ | 204/403.09 |
| 5,965,380 A | 10/1999 | Heller et al. | |
| 5,985,129 A | 11/1999 | Gough et al. | |
| 5,992,211 A | 11/1999 | Skrtic | |
| 6,001,067 A | 12/1999 | Shults et al. | |
| 6,002,954 A | 12/1999 | Van Antwerp et al. | |
| 6,027,479 A | 2/2000 | Alei et al. | |
| 6,049,727 A | 4/2000 | Crothall | |
| 6,051,389 A | 4/2000 | Ahl et al. | |
| D424,696 S | 5/2000 | Ray et al. | |
| D426,638 S | 6/2000 | Ray et al. | |
| 6,093,167 A | 7/2000 | Houben et al. | |
| 6,103,033 A | 8/2000 | Say et al. | |

(Continued)

FOREIGN PATENT DOCUMENTS

| | | |
|---|---|---|
| WO | WO 97/19188 | 5/1997 |
| WO | WO 99/66964 | 12/1999 |
| WO | WO 01/01851 A1 | 11/2001 |

OTHER PUBLICATIONS

EP Search Report as issued in International Application No. 02763782.6-2402, Mailing date Oct. 18, 2005.
Elsevier Science B.V. 1996 (XP-002347586)—Analytica Chimica Acta (Glucose-sensitive ion-sensitive field-effect transistor-based biosensor with additional positively charged membrane Dynamic range extension and reduction of buffer concentration influence on the sensor response. (pp. 77-81).

(Continued)

*Primary Examiner* — David Naff

(74) *Attorney, Agent, or Firm* — Foley & Lardner

(57) ABSTRACT

A method for formulating and immobilizing a protein and a protein matrix formed by the method. The protein matrix preparation method results in a physically and chemically stable protein matrix that has low swelling, non-leaching, high activity, and high mechanical strength properties. The method includes cross-linking and hardening the protein mixture and using a mold to form a protein into a desired shape and size.

26 Claims, 12 Drawing Sheets

U.S. PATENT DOCUMENTS

| | | |
|---|---|---|
| 6,120,676 A | 9/2000 | Heller et al. |
| 6,122,536 A | 9/2000 | Sun et al. |
| 6,125,290 A | 9/2000 | Miesel |
| 6,125,291 A | 9/2000 | Miesel et al. |
| 6,134,459 A | 10/2000 | Roberts et al. |
| 6,135,978 A | 10/2000 | Houben et al. |
| 6,144,866 A | 11/2000 | Miesel et al. |
| 6,159,240 A | 12/2000 | Sparer et al. |
| 6,162,611 A | 12/2000 | Heller et al. |
| 6,163,723 A | 12/2000 | Roberts et al. |
| 6,171,586 B1 | 1/2001 | Lam et al. |
| 6,175,752 B1 | 1/2001 | Say et al. |
| 6,198,952 B1 | 3/2001 | Miesel |
| 6,201,980 B1 | 3/2001 | Darrow et al. |
| 6,248,080 B1 | 6/2001 | Miesel et al. |
| 6,251,260 B1 | 6/2001 | Heller et al. |
| 6,261,280 B1 | 7/2001 | Houben et al. |
| 6,267,958 B1 | 7/2001 | Andya et al. |
| 6,268,161 B1 | 7/2001 | Han et al. |
| 6,280,587 B1 | 8/2001 | Matsumoto |
| 6,343,225 B1 * | 1/2002 | Clark, Jr. ................ 600/347 |
| 2002/0127623 A1 | 9/2002 | Minshull et al. |

OTHER PUBLICATIONS

Witt, S. et al. Conserved arginine-516 of penicillium amagasakiense glucose oxidase is essential for the efficient binding of B-D glucose. Biochem. J. 2000, pp. 553-559, see entire document.

Elias, M.D. et al. Functions of amino acid residues in the active sit of *Escherichia coli* pyrroloquinoline quinone containing quinoprotein glucose dehydrogenase. The Journal of Biological Chemistry. Mar. 2000, vol. 275, No. 10, pp. 7321-7326, see entire document.

PCT International Search Report as issued in International Application No. PCT/US02/30942, Mailing date Jun. 19, 2003.

* cited by examiner

Placement of the Biomechanical Pancreas in a Human Subject

SWELLING STUDIES

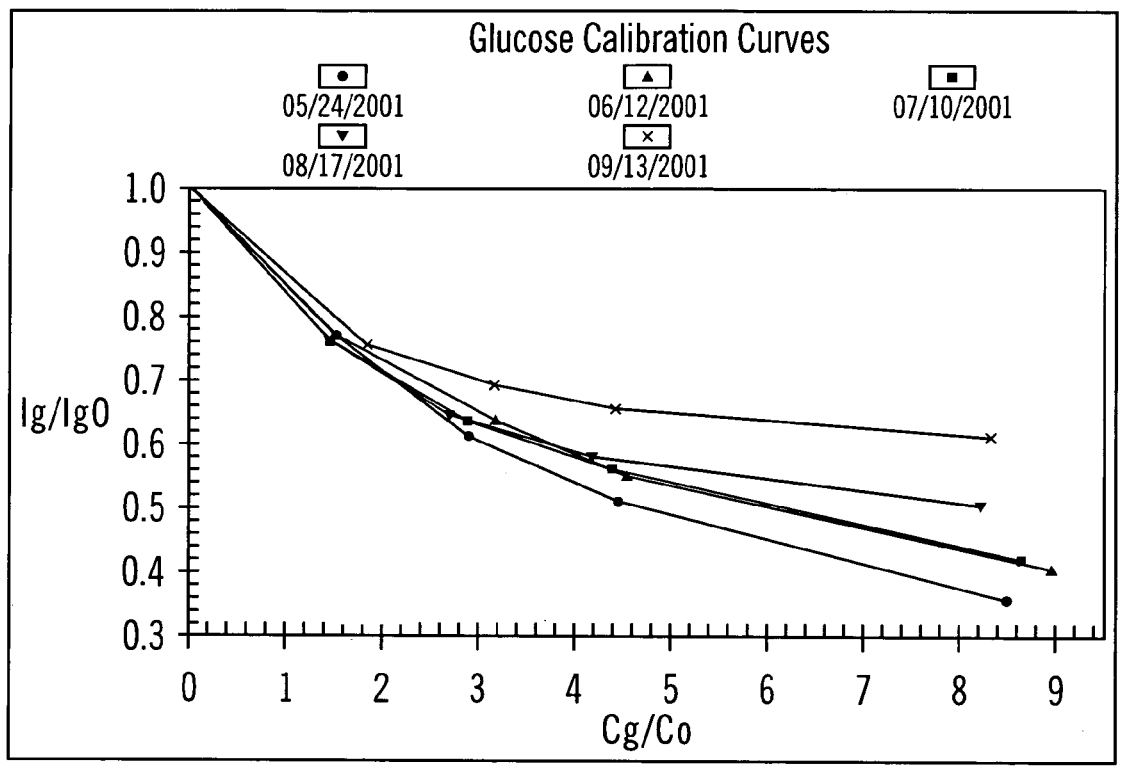
FIG. 8A  Sensor Using SMP With No Silicone Additive
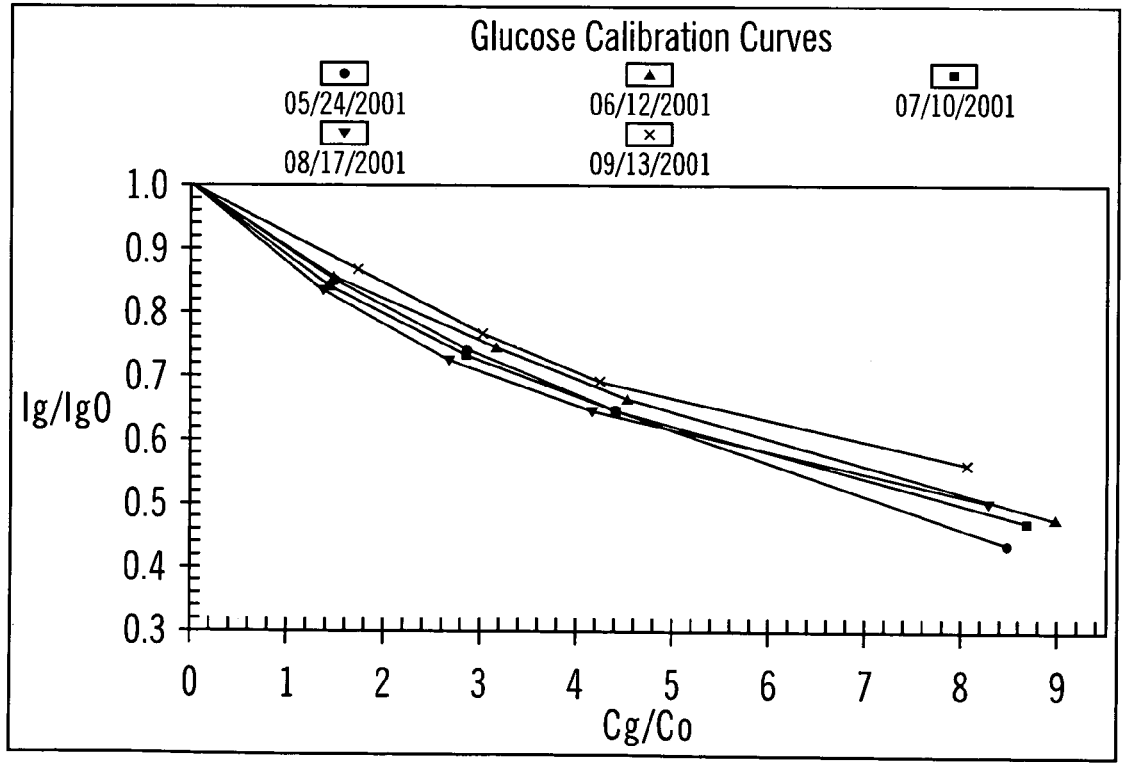
FIG. 8B  Sensor Using SMP With Silicone Additive

MOLDED PROTEIN MATERIAL IN FORM OF PELLET FOR SENSOR

CROSS-REFERENCE TO RELATED APPLICATIONS

This application is a divisional of application Ser. No. 10/033,723, filed Dec. 27, 2001, now U.S. Pat. No. 7,192,766 which is in turn claims the benefit of prior filed U.S. Provisional Application Ser. Nos. 60/335,663 filed Oct. 23, 2001. The entirety of each which are incorporated herein by reference. This listing of claims will replace all prior versions, and listings, of claims in the application.

BACKGROUND

1. Field of the Invention

The present invention relates, generally, to methods and systems for formulating and immobilizing a protein matrix and/or enzyme and, in particular embodiments, to immobilizing proteins or enzymes that are physically and chemically stable over time, for example, for use in short-term or long-term sensors and biosensors.

2. Description of Related Art

The combination of biosensors and microelectronics has resulted in the availability of portable diagnostic medical equipment and has improved the quality of life for countless people. Many people suffering from disease or disability who, in the past, were forced to make routine visits to a hospital or a doctor's office for diagnostic testing currently perform diagnostic testing on themselves, in the comfort of their own homes, using equipment with accuracy to rival laboratory equipment.

Nonetheless, challenges in the biosensing field have remained. For example, although many diabetics currently utilize diagnostic medical equipment in the comfort of their own homes, the vast majority of such devices still require diabetics to draw their own blood and to inject their own insulin. Drawing blood typically requires pricking a finger. For someone who is diagnosed with diabetes at an early age, the number of self-induced finger-pricks and insulin injections over the course of a lifetime could reach into the tens of thousands. Drawing blood and injecting insulin thousands of times can be overtly invasive and inconvenient, as well as painful and emotionally debilitating.

Diagnostic requirements of those with disease or disability may be addressed by using a sensing apparatus that may be implanted into the body and that may remain in the body for an extended period of time. For example, an implantable sensing and infusion system is disclosed in pending U.S. patent application No. 60/318,060, incorporated herein by reference. An example of the type of implantable sensing system described in that application is illustrated in FIG. 1 herein. The sensing system illustrated in FIG. 1 comprises an implantable infusion pump 12 with a catheter 20 for dispensing an infusion formulation and a lead 14 connecting the infusion pump to a sensing device 16. The sensing device 16 may be inserted into a vein, an artery, or any other part of a human body where it could sense a desired parameter of the implant environment. A window may be provided in the sensing device 16 to facilitate sensing. An active sensing matrix 18, such as an enzyme, may be placed inside of the sensing device 16. The matrix 18 may be any of a variety of enzymes, proteins, or the like, that may be employed for sensing. For example, if physiological parameter sensing is desired, one or more proteins may be used as the enzyme. More specifically, if the device is a glucose-sensing device, for example, a combination of glucose oxidase (GOx) and human serum albumin (HSA) may be used concurrently in a solid matrix form to form a sensor matrix protein.

Previous processes for formulating an enzyme for use in a sensor involved placing the enzyme into a cavity within a sensing device while the enzyme was still in a liquid or gel-like form. In such processes, the gel-like enzyme would be placed into the sensing device cavity, where it would harden in place, within the cavity. A hardening or cross-linking reagent would be added to the enzyme to cause solidification of the enzyme once it was inside the sensing device.

One of the difficulties associated with conventional processes is that of producing protein matrices that are sufficiently chemically stable over time. For example, in the case of glucose biosensors, it has been found that GOx undergoes oxidative inactivation by peroxide and oxygen over time. Since the lifetime of glucose sensors primarily depends on the lifetime of the GOx, the sensitivity of the sensors is lost over time as the enzyme decays. Glucose oxidase goes through a cycle of oxidation and reduction upon interaction with glucose. Glucose oxidase is most vulnerable to deactivation in its reduced state. Hydrogen peroxide, hydroperoxy radicals, and the like, can deactivate GOx, particularly in its reduced state. The glucose oxidase reaction sequence is more thoroughly described and illustrated in FIG. 5.

An additional problem with conventional processes for formulating protein matrices for use in sensing devices is that the sensor matrix protein may not be sufficiently stable mechanically over time. In the case of glucose biosensors, for example, there has been a problem of the GOx not possessing the desired mechanical stability, i.e., that the GOx maintain its shape. Enzymes produced by conventional processes can be susceptible to swelling or shrinking. For example, a conventional process of injecting a GOx solution or gel into a cavity of a sensor body and then hardening the GOx in place can result in shrinkage and disfigurement of the GOx enzyme during hardening. As a result, each sensor produced according to such processes may have a different shaped GOx enzyme and, thus, may behave somewhat different than other sensors made according to the same process. In addition, enzymes can be susceptible to leaching. Sensor accuracy and sensitivity can be adversely affected when the enzyme utilized in the sensor is susceptible to leaching or swelling. Indeed, swelling of the enzyme over time can cause the sensor body to deform. Deformation of the body of the sensor may alter the response or the calibration of the sensor. Moreover, a swelling or leaching of the enzyme may cause the shape of the window in the sensing device to change which also could alter the response of the sensing device.

Further problems have been associated with the process of injecting an enzyme into a sensing device while the enzyme is in a gel form. When an enzyme is injected into a cavity of a sensing device, it is difficult to ensure that the enzyme has filled the volume in the sensing device completely. If there are voids left in the cavity after the enzyme has been injected, those voids can adversely affect the stability and sensitivity of the sensing device. Moreover, since the enzyme may tend to shrink as it hardens or solidifies, further voids or spaces may be left in the enzyme cavity of the sensor.

SUMMARY OF THE DISCLOSURE

Therefore, it is an advantage of embodiments of the present invention to provide a process for combining protein formulation and immobilization techniques which result in a physically and chemically stable protein matrix.

It is a further advantage of the embodiments of the present invention to provide a method for formulating and immobilizing a protein matrix that is molded into a desired shape and size before it is inserted into a sensing device. Embodiments of the present invention comprise a protein matrix and processes for making protein matrices having improved mechanical stability as a result of hardening and cross-linking procedures carried out before the enzyme is placed inside of a sensing device.

It is a further advantage of the embodiments of the present invention to provide a method for formulating and immobilizing a protein matrix in which retained activity, mechanical stability, and operational stability may be customized to a diagnostic or continuous sensing application by changing the enzyme or protein and by changing the cross-linking process parameters.

It is a further advantage of embodiments of the present invention to provide methods for formulating and immobilizing protein matrices that have sufficiently low swelling and leaching properties as well as sufficiently high activity and mechanical strength properties. Embodiments of the formulation and immobilization methods may be applied to prepare a protein matrix for use in short-term or long-term sensors and biosensors. Moreover, embodiments of the method could be utilized to mold proteins for uses other than sensing devices, such as, for example, the molding of biological tissue replacement, arteries, heart valves, or the like.

It is a further advantage of embodiments of the present invention to provide a method for formulating and immobilizing a protein matrix to be used in an implantable sensing device that can operate in a sufficiently consistent and invariant manner, without appreciably losing its sensitivity over an extended period of time.

It is a further advantage of embodiments of the present invention to provide a protein pellet that has a sufficiently high concentration of GOx. By increasing the GOx concentration, embodiments of the present invention may counteract the effects of enzyme decay and extend the life of a sensing device. According to such embodiments, a protein pellet is hardened and molded into the desired shape and size before being inserted into a sensing device, for example, to ensure proper fit and to reduce the likelihood of swelling or leaching. FIG. 7 shows two graphs illustrating the results of a swelling analysis. The first graph shows the swelling of a glucose oxidase-human serum albumin matrix formulated with insufficient immobilization. The second graph shows the swelling properties of the matrix formulated with improved immobilization according to embodiments of the present invention.

In one embodiment of the present invention, a method comprises combining a protein mixture (such as, but not limited to, GOx and human serum albumin (HSA)) with a cross-linking reagent (such as, but not limited to, glutaraldehyde). In this embodiment, the mixture is injected into a mold where it is hardened. Once hardened, the immobilized enzyme, protein, or other such matrix, may be further cross-linked with glutaraldehyde or another cross-linking reagent, to give a mechanically stable protein. The type of cross-linker and the extent of immobilization may vary depending on the enzyme, protein, or the like. The hardened protein mixture can be cut, machined, or otherwise formed to the desired shape and size. In one embodiment, the mold is configured to shape the mixture into semi-cylindrical rope-like structures that are subsequently cut into pellets. It has been found that sensing devices utilizing a protein pellet produced by this method can exhibit improved longevity.

In another embodiment of the present invention, a method for formulating and immobilizing the protein matrix further comprises adding silicone particles to the protein matrix. The addition of silicone particles is believed to discourage the depletion of oxygen in the sensing device. Oxygen depletion causes GOx to be in its reduced state. Reduced GOx is more vulnerable to deactivation. Accordingly, the addition of the silicone may further contribute to the chemical stability of the sensor matrix protein over time.

These and other objects, features, and advantages of embodiments of the invention will be apparent to those skilled in the art from the following detailed description of embodiments of the invention, when read with the drawings and appended claims.

BRIEF DESCRIPTION OF THE DRAWINGS

A brief description of preferred embodiments of the invention will be made with reference to the accompanying drawings wherein:

FIG. 8a shows a graph that illustrates a glucose calibration curve for a sensor without an additive.

FIG. 8b shows a graph that illustrates a glucose calibration curve for a sensor incorporating a silicone additive according to an embodiment of the invention.

DETAILED DESCRIPTION OF PREFERRED EMBODIMENTS

Figure 1A:
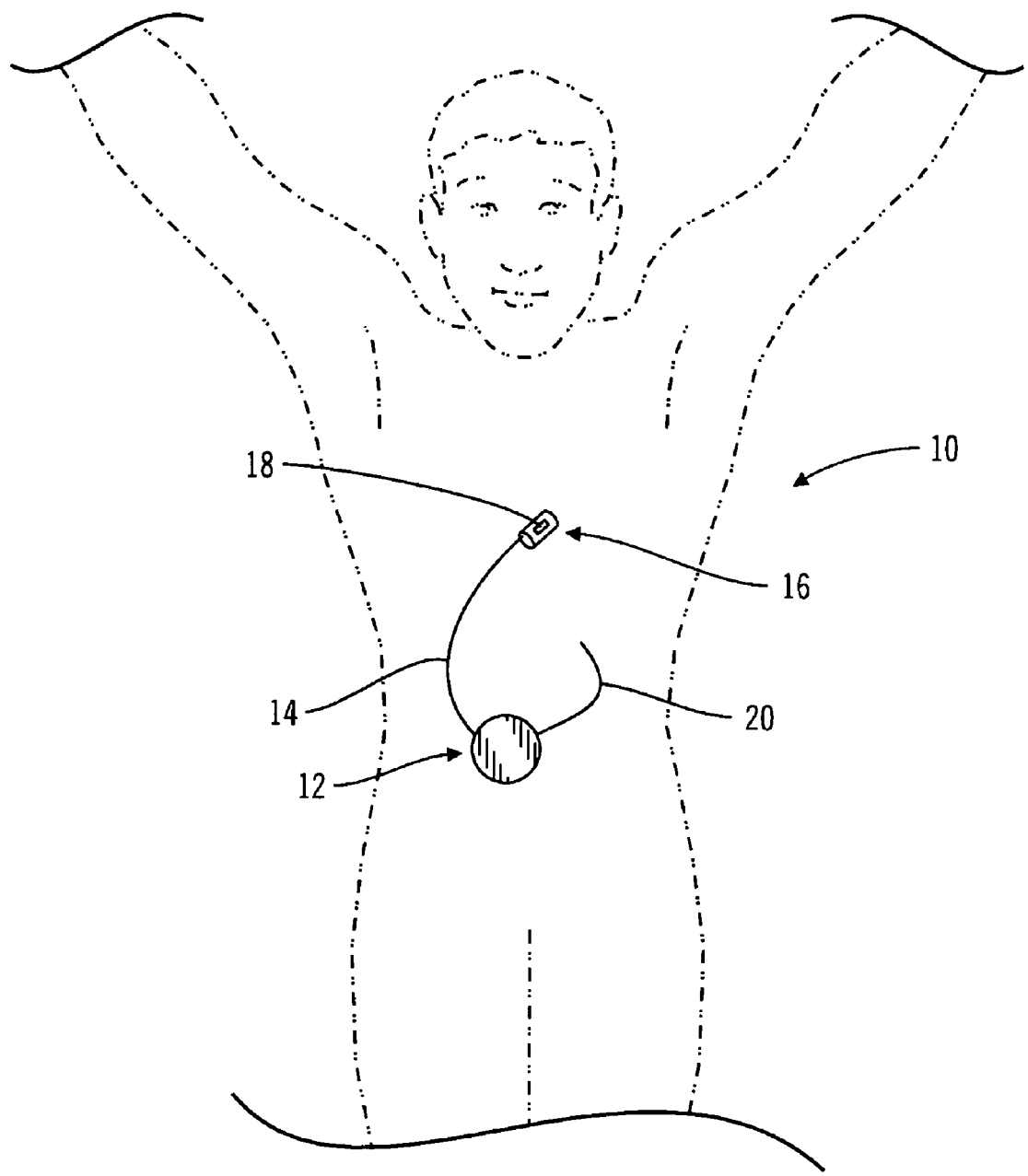
FIG. 1a shows a fragmented cutaway view of an exemplary environment of use of an implantable sensing device (not shown to scale) in which a sensor matrix protein (not shown to scale) according to an embodiment of the present invention may be utilized.

The following detailed description is of the best presently contemplated mode of carrying out the invention. This description is not to be taken in a limiting sense, but is made merely for the purpose of illustrating the general principles of the invention. The scope of the invention is best defined by the appended claims.

The present invention relates, generally, to protein matrices and/or enzymes and processes for formulating and immobilizing protein matrices and/or enzymes. As discussed above, such a protein matrix may facilitate, for example, the creation of long-lived and stable sensors. In an example embodiment, the protein matrix is an immobilized glucose oxidase (GOx) and human serum albumin (HSA) matrix for use in glucose biosensors. However, further embodiments of the invention involve molding other proteins for a variety of purposes. Processes according to the various embodiments of the invention may be employed to produce physically and chemically stable protein matrices.

FIG. 1 illustrates an example of a system 10 in which a sensor matrix protein produced pursuant to an embodiment of the invention may be utilized. Other embodiments may employ other suitable system configurations. However, by way of example, the system 10 in FIG. 1 includes an implantable infusion pump 12 which may be implanted in a patient's body, such as in a patient's abdomen. The pump 12 dispenses an infusion formulation (e.g., an insulin formulation) via a catheter 20. A lead 14 connects the pump 12 to a sensing device 16 for regulating the delivery of the infusion formulation dependent upon a sensed parameter of the implant environment. In the sensor system in FIG. 1, a protein pellet 18 is employed as a protein matrix within the sensing device 16. The sensing device. 16 may be any suitable sensor that operates with an active protein or enzyme, including, but not limited to, the sensors described in U.S. patent application No. 60/318,060, which is incorporated herein by reference.

Figure 1B:
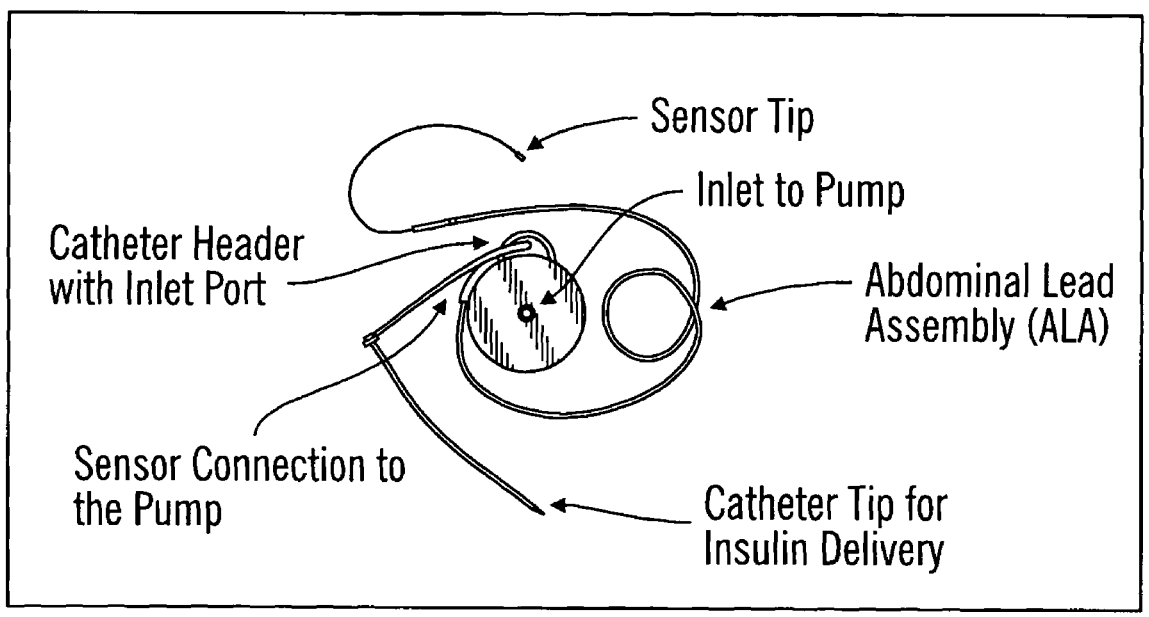
FIG. 1b shows a two-dimensional view of an implantable infusion and sensing device.
Figure 1C:
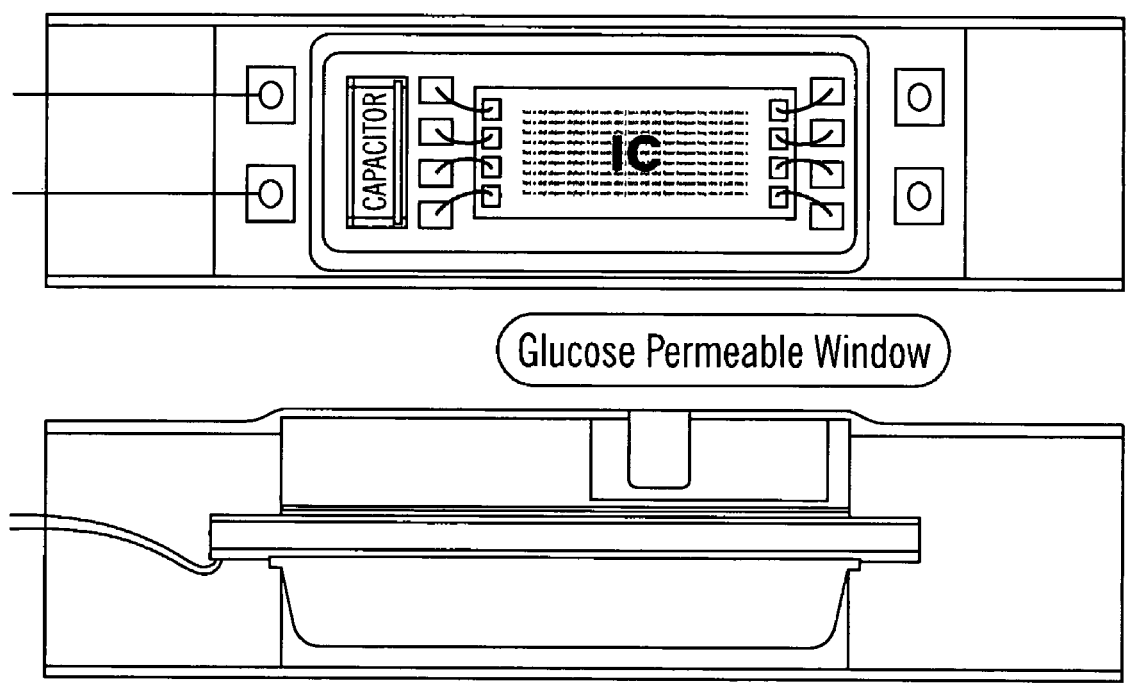
FIG. 1c shows a cutaway expanded view of a sensor region of a sensing device.
Figure 1D:
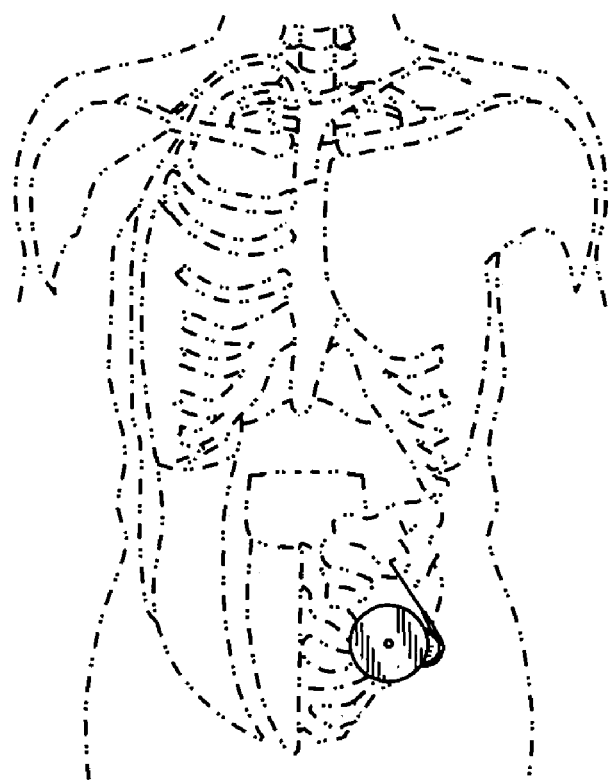
FIG. 1d shows another fragmented cutaway view of an exemplary environment of use of an implantable sensing device.

FIG. 1b shows a two-dimensional view of the system 10 that is illustrated in FIG. 1a. FIG. 1c shows an expanded cutaway view of the sensor region of the infusion and sensing system illustrated in FIGS. in 1a and 1b.

Figure 2A:
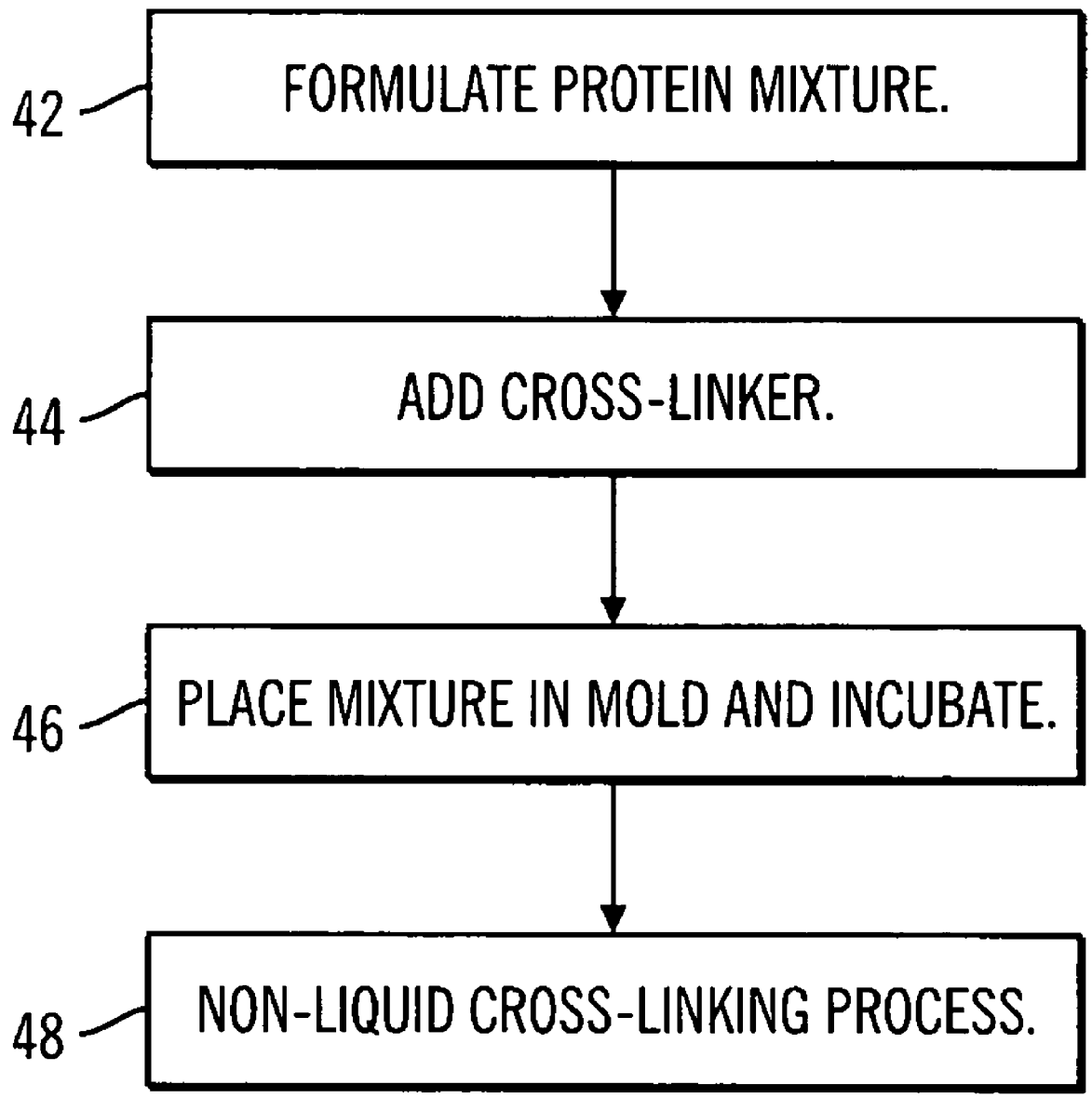
FIG. 2a shows flowchart diagram of a method for formulating and immobilizing a sensor matrix protein according to one embodiment of the invention.

FIG. 2a illustrates in a flow diagram, a process according to an embodiment of the present invention for producing a protein matrix. According to the process, a protein mixture is first obtained or formulated. The protein mixture may be one that is free of polymeric additives and one that is concentrated using ultrafiltration or other chromatographic techniques. A protein matrix may then be formed by adding a cross-linking agent to the protein mixture and then placing the polymerizing mixture into a mold. The formed matrix is then placed in a non-liquid atmosphere containing a cross-linking agent in order to maintain compositional integrity and to achieve the desired ultimate mechanical properties. Retained activity, mechanical stability, and operational stability can be customized according to a diagnostic or continuous sensing application by changing the protein and cross-linking process parameters. A more detailed description of a specific embodiment of the invention is described below in connection with FIG. 2b.

Figure 2B:
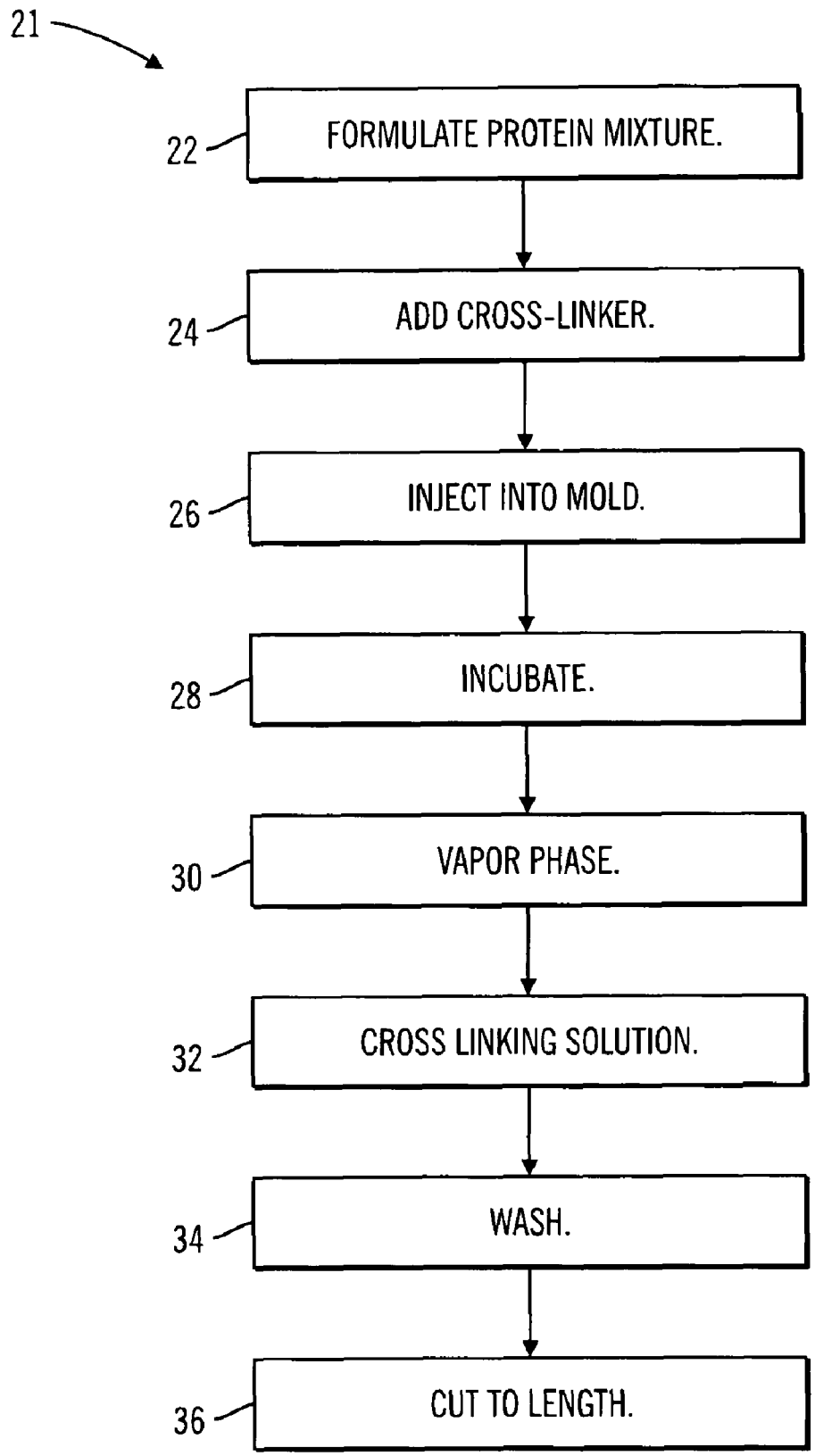
FIG. 2b shows a flowchart diagram of a method for formulating and immobilizing a sensor matrix protein according to one embodiment of the invention.

FIG. 2b illustrates in a flow diagram, a process according to an embodiment of the present invention for producing a protein pellet 18. The embodiment illustrated in FIG. 2b is a process for formulating and immobilizing a sensor matrix protein. In preferred embodiments, the method may be employed to yield protein pellets that are mechanically and chemically stable over time and that can be inserted, in their hardened state, into sensing devices.

In the embodiment illustrated in FIG. 2b, initially, a protein mixture or suspension is obtained or formulated, as shown at 22. In the example embodiment, the protein mixture that is obtained or formulated is one that is free of polymeric additives and concentrated using ultrafiltration or other chromatographic techniques. In an example embodiment, the protein mixture comprises a GOx and HSA mixture. The GOx concentration may vary for different embodiments of the invention. For example, the GOx concentration may be within the range of approximately 350 mg/ml (67,000 U/ml) to approximately 700 mg/ml (150,000 U/ml). In such embodiments, the HSA concentration may vary between about 23-32.5% (w/v), depending on the GOx concentration. Or, collagen or other structural proteins could be used instead of or in addition to HSA.

For embodiments employing enzymes other than GOx, concentrations other than those discussed herein may be utilized. For example, depending on the enzyme employed, concentrations ranging from approximately 10% weight per weight to 70% weight per weight may be suitable. The concentration may be varied not only depending on the particular enzyme being employed, but also depending on the desired properties of the resulting protein matrix. For example, a certain concentration may be utilized if the protein matrix is to be used in a diagnostic capacity while a different concentration may be utilized if certain structural properties are desired. Those skilled in the art will understand that the concentration utilized may be varied through experimentation to determine which concentration (and of which enzyme or protein) may yield the desired result.

Although GOx is employed in the embodiment described herein, other proteins and/or enzymes may also be used or may be used in place of GOx, including, but not limited to, hexose oxidase, lactate oxidase, and the like. Other proteins and/or enzymes may also be used, as will be evident to those skilled in the art. Moreover, although HSA is employed in the example embodiment, other structural protein, such as collagen or the like, could be used instead of or in addition to HSA.

Next, a cross-linking reagent is added to the protein mixture as shown at 24. In one embodiment, an amine cross-linking reagent, such as, but not limited to, glutaraldehyde, is added to the protein mixture. The addition of a cross-linking reagent to the protein mixture creates a protein paste. The concentration of the cross-linking reagent to be added may vary according to the concentration of the protein mixture. In an example embodiment, the GOx concentration may be about 67,000 U/ml and the HSA concentration may be about 25% (w/v), while the final glutaraldehyde concentration in the enzyme matrix may be approximately 1.25%.

Although glutaraldehyde is utilized in the embodiment described above, other cross-linking reagents may also be used or may be used in place of glutaraldehyde, including, but not limited to, an amine reactive, homofunctional, cross-linking reagent such as Disuccinimidyl Suberate (DSS). Another example is 1-Ethyl-3 (3-Dimethylaminopropyl) Carbodiimide (EDC), which is a zero-length cross-linker. EDC forms an amide bond between carboxylic acid and amine groups. Other suitable cross-linkers also may be used, as will be evident to those skilled in the art.

Once a cross-linking reagent is added to the protein mixture, the combined mixture can be injected into or otherwise applied to a mold. This may be done, for example, by drawing the combined mixture into a syringe and injecting the mixture into a mold. In some embodiments, the combined mixture may be highly reactive, and thus, may harden quickly. Therefore, the combined mixture should be injected into, or otherwise applied to, the mold quickly before the mixture hardens.

The shape or form of the mold may be dependent on the desired size and shape of the resulting protein pellet. For example, the mold could be configured to produce a protein pellet that is precisely the desired shape and size. However, the mold may also be configured to yield a protein matrix that still needs to be cut, machined, or otherwise formed to the desired shape and size.

Figure 3:
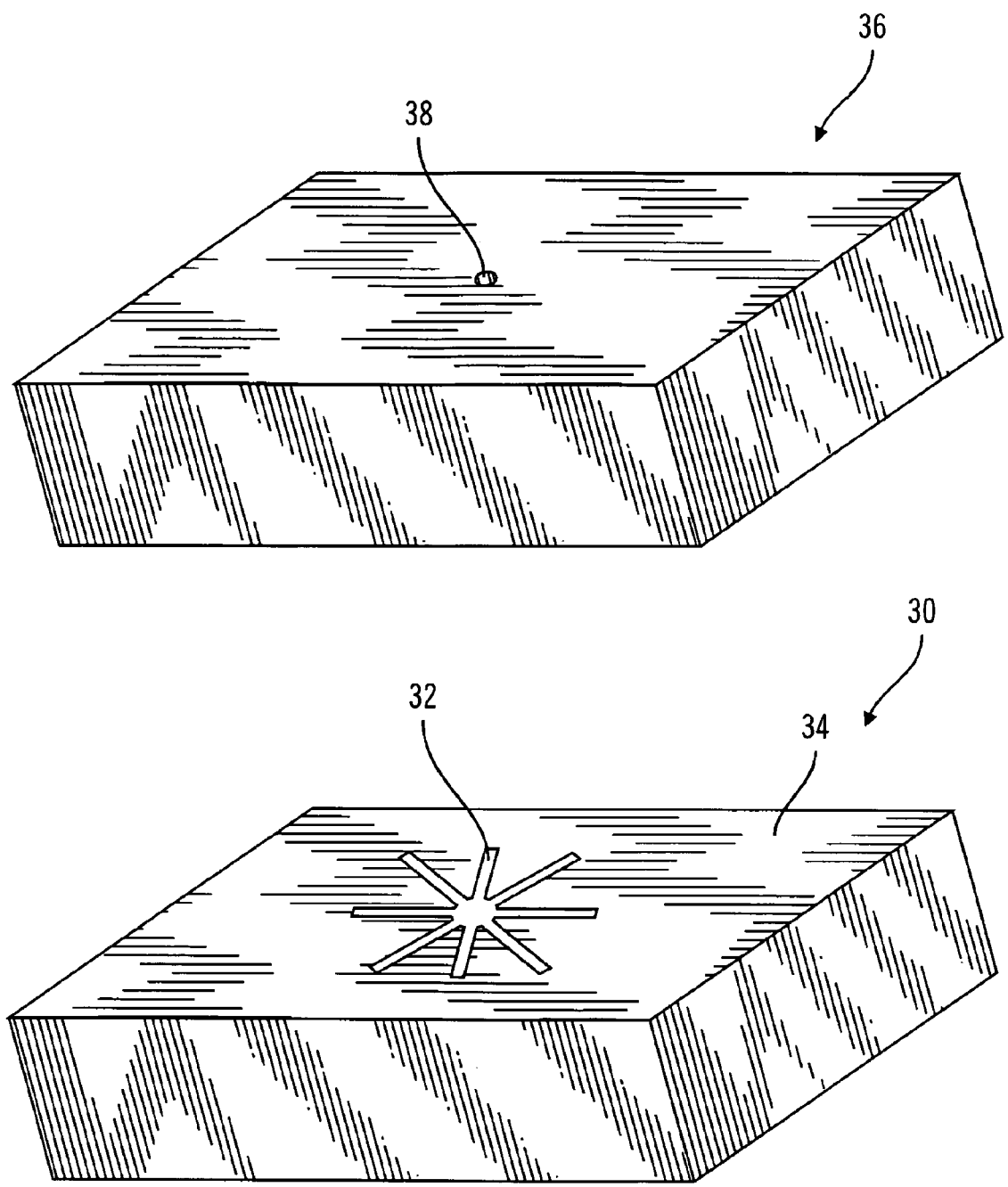
FIG. 3 shows a perspective view of an example of a mold utilized in one embodiment of the invention.
Figure 4A:
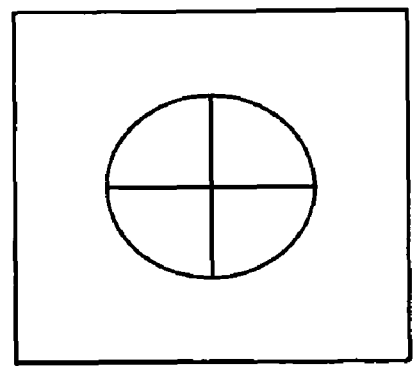
FIGS. 4a through 4d show two-dimensional views of examples of molds utilized in other embodiments of the invention.
Figure 4B:
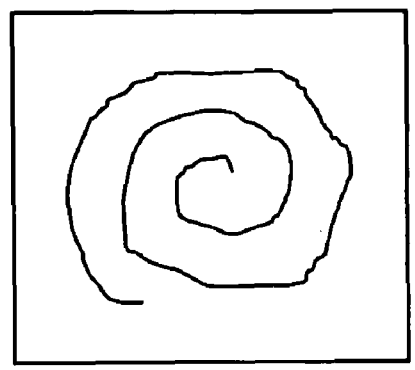
Figure 4C:
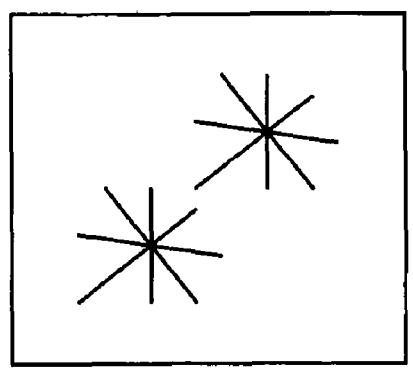
Figure 4D:
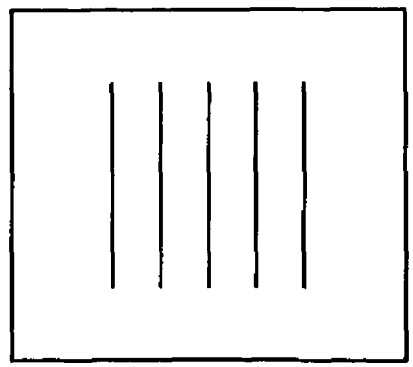
Figure 5:
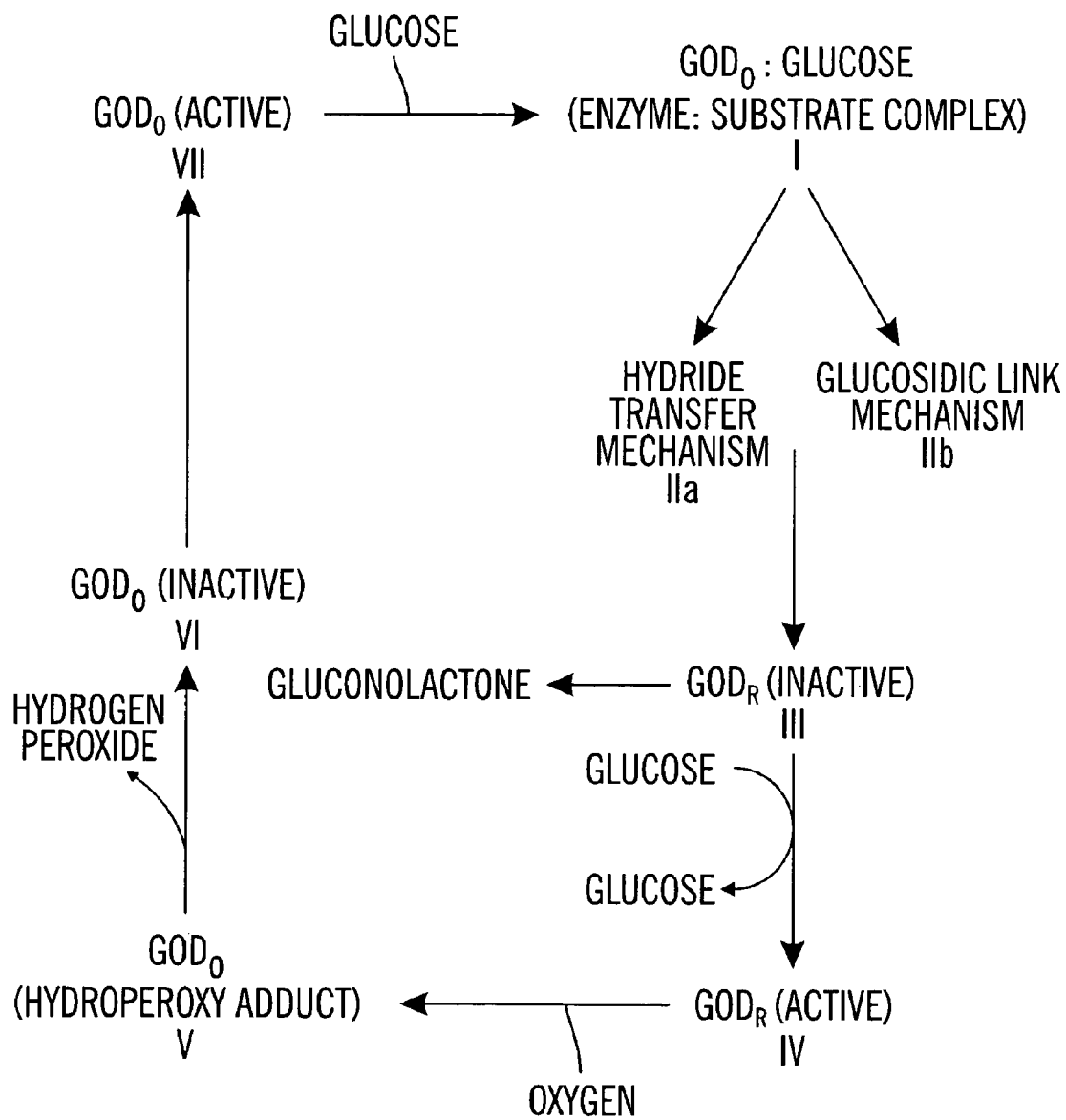
FIG. 5 shows a flow diagram of a glucose oxidase reaction sequence.
Figure 6:
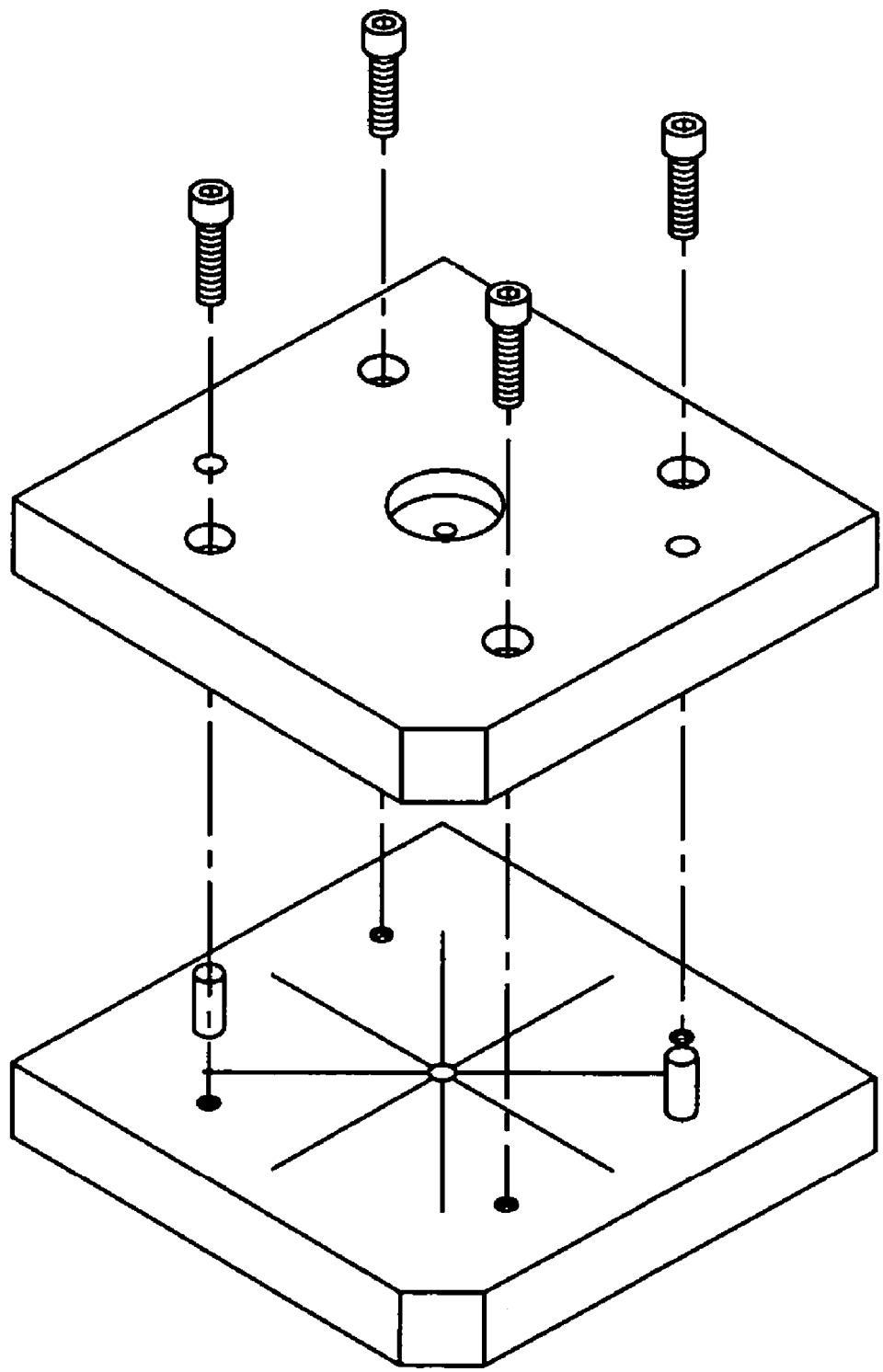
FIG. 6 shows a perspective view of another example of a mold that may be utilized in an embodiment of the invention.
Figure 7A:
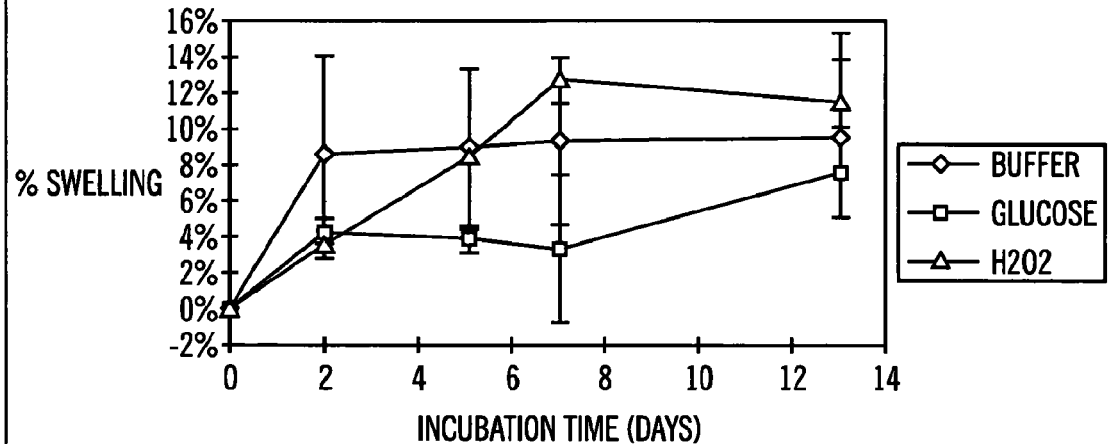
FIG. 7 shows two graphs depicting the results of a swelling analysis done on a glucose oxidase-human serum albumin matrix, first showing the swelling with insufficient immobilization of the matrix, and second showing the swelling with the improved immobilization process according to embodiments of the invention.
Figure 7B:
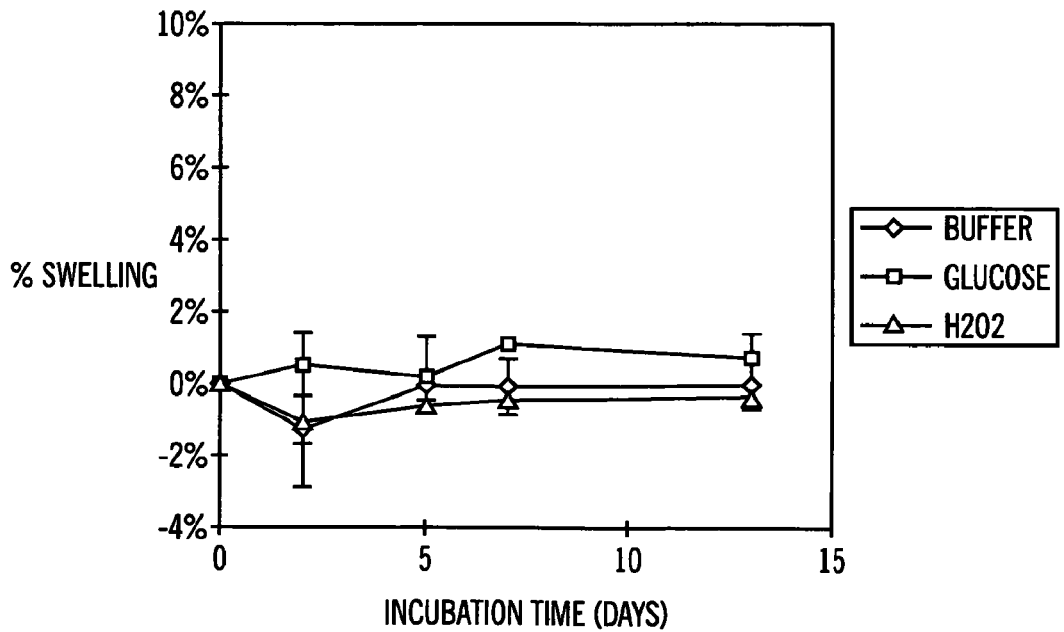

FIG. 3 shows a perspective view of one example of a mold that can be utilized in accordance with an embodiment of the invention. The mold may be formed to have a chemically inert surface. One way to insure that the mold has a chemically inert surface is to use materials such as, but not limited to, teflon, delrin, and the like. The mold in the illustrated embodiment is comprised of two opposing blocks 30 and 36. In the illustrated orientation, the bottom block 30 has intersecting channels 32 on its top surface 34. The intersecting channels 32 are each formed by semicylindrical recesses in the top surface 34 of the bottom block 30. A top block 36 has a flat bottom surface. In the illustrated embodiment, the top surface 34 of the bottom block 30 and the bottom surface of the top block 36 are pressed or screwed together. The protein mixture may be injected into the mold through an opening or hole 38 that passes all the way through the top block 36.

Other embodiments may employ molds of varying configurations. Variations that may be employed in other embodiments are illustrated in FIGS. 4a-4d. As is illustrated in FIGS. 4a-4d, the recesses (or channels) in the mold may be configured differently. For example, the recesses could be parallel lines, a spiral, or multiple groups of intersecting lines. Also, although the embodiment described herein employs recesses (or channels) that are semicylindrical, other suitable shapes or channel cross-section configurations could be employed. The cross-section configuration may be varied according to the desired application. For example, the channel cross-sections could be rectangular, cylindrical, tubular, spherical, or any other desired or suitable configuration. Other suitable application specific mold configurations will be apparent to those skilled in the art.

Once the combined mixture has been placed in the mold, the mixture is incubated in the mold. In one example embodiment, the mixture is incubated at room temperature for approximately two hours. Following the incubation period, the mixture may be cross-linked, but it may not yet be fully hardened. In other embodiments, the incubation may be carried out for other suitable time periods and/or may be carried out at an elevated temperature. The primary form may be imparted to the protein matrix during this initial molding operation. In other words, the mold may define the ultimate shape of the protein matrix.

Following incubation, the protein matrix then may be placed in an atmosphere containing a cross-linking agent in order to maintain the compositional integrity and achieve ultimate mechanical properties. In the example embodiment, after incubation, the mixture is exposed to a vaporized cross-linking reagent. However, in other embodiments, other non-liquid-based environments may be utilized. The non-liquid cross-linking process further hardens and solidifies the mixture. Those skilled in the art will understand that suitable non-liquid environments that range from very high pressure to very low pressure may be suitable. The environment's temperature could also be varied according to experimentation.

In the example embodiment, the non-liquid cross-linking process may be done by opening the mold and exposing the mixture to a vapor phase in a reactor for a suitable time period to further harden and solidify the mixture. In an example embodiment in which the mold is configured as illustrated in FIG. 3, the two blocks of the mold may be separated after which the mixture may still reside in the recesses 32 of the block 30. The block 30, with the mixture still in the recesses 32, may then be placed into a chamber in a vapor phase reactor. In one example embodiment, the mixture, while still in the recesses 32 of the opened mold, is exposed to vapor phase for approximately 16 hours. In other embodiments, other suitable exposure time periods may be employed. The vapor phase cross-linking reagent may comprise, for example, approximately 12.5% (w/w) glutaraldehyde in a water vapor. In other embodiments, other suitable vapor phase cross-linking reagents may be employed. The inclusion of a water vapor in the vapor phase may be desirable in contexts in which the protein mixture should remain hydrated. For example, enzymes may cease to be active if the reactor is dry.

In an example embodiment, after the mixture has been exposed to the vaporized cross-linking reagent for a suitable period of time, the mixture may be removed from the mold and introduced to or placed in a cross-linking solution to further cross-link the hardened mixture. The mixture may, at this point in the process, resemble the configuration of the recesses in whatever type of mold was employed in the process. For example, if a mold as shown in FIG. 3 was employed, then at this point in the process, the hardened mixture will resemble semi-cylindrical rope-like structures. In the example embodiment in FIG. 2, after further cross-linking the GOx-HSA matrix with vapor glutaraldehyde, the hardened ropes may be exposed to a 2.5% buffered glutaraldehyde solution. The glutaraldehyde in the solution may react with remaining or residual amine groups to further cross-link the GOx-HSA matrix. Other embodiments might employ glutaraldehyde solutions with suitable concentrations varying, as required, according to the proteins or enzymes utilized. Further embodiments might use cross-linking solutions with cross-linking reagents other than glutaraldehyde, such as, but not limited to, EDC and DCC, and the like. In an example embodiment, the hardened mixture is submerged in the cross-linking solution for approximately one hour. In other embodiments, other suitable time periods may be employed. Moreover, those skilled in the art will understand that this part of the process could be omitted in other embodiments.

In an example embodiment, after the hardened mixture has been introduced to or placed in the cross-linking solution, then the hardened mixture is washed. In an embodiment where the hardened mixture was not placed in a cross-linking solution at all, then the hardened mixture may be washed after the vapor phase. The hardened mixture may be washed in a variety of washing solutions, including but not limited to, phosphate buffered saline (PBS), sterile deionized water, or any other suitable washing solution. Moreover, the hardened mixture may be washed a single time or it may be washed more than one time. In an example embodiment, the hardened mixture is washed five times with sterile deionized water, phosphate buffered saline, and/or glycine buffer. The purpose of washing the hardened mixture is to remove any residual glutaraldehyde. In other embodiments, methods other than washing could be employed to remove residual glutaraldehyde, or to remove residual amounts of a different cross-linking reagent that might have been employed, without deviating from the spirit or scope of the invention. In other embodiments, the washing process or the removal of residual amount of cross-linking reagents by other means, could be omitted entirely.

In the example embodiment, after the hardened mixture has been washed, it may then be cut, machined, or otherwise formed into pieces that are the desired shape and size. The hardened mixture may be easily cut at this point in the process. As discussed above, in an example embodiment, the desired form for the sensor matrix protein is a semi-cylindrical pellet structure. The example mold illustrated in FIG. 3 yields rope-like structures that may be cut into pellet-sized pieces. The primary structure or form for the protein matrix is imparted during the initial molding operation. Accordingly, the cutting or machining process could take place, for example, before the vapor phase, or at any other point in the process after the mixture has been incubated in the mold.

In other embodiments, a mold may be employed which forms the mixture to the desired shape and size (i.e., a semi-cylindrical pellet structure). Of course, if an embodiment employs a mold that forms the mixture to the desired shape and size, then the mixture would not need to be cut, machined, or otherwise formed as a part of the process. In that case, cutting, machining, or otherwise forming the mixture may be omitted from the process. Moreover, in the example embodiment, the resulting pellet is sized to be a line-to-line fit for a sensor in which it may be placed. In another embodiment, the mixture may be molded such that it is slightly oversized to insure a snug fit within a device into which it might be placed, such as, but not limited to, a sensing device.

It is an advantage of an embodiment of the invention that the concentration of GOx is maximized so as to extend the life of a sensor. In other embodiments of the invention, the Gox concentration is increased to further extend the life of a sensor.

For example, in another embodiment, the same procedure described above and illustrated in FIG. 2 may be utilized. However, the concentrations of GOx, HSA, and glutaraldehyde may be varied. For example, an embodiment might employ a GOx concentration of approximately 100,000 U/ml with a HSA concentration of approximately 32.5% (w/v). In such an embodiment, the GOx-HSA mixture may be immobilized with approximately 100 µl of a 12.5% (w/w) glutaraldehyde solution. Such an embodiment may yield a protein pellet that remains physically and chemically stable for approximately one year.

In another embodiment, the same procedure described above and illustrated in FIG. 2 may be utilized employing a GOx concentration of approximately 135,000 U/ml with an HSA concentration of approximately 23% (w/v). In such an embodiment, the GOx-HSA mixture may be immobilized with approximately 100 µl of a 25% (w/w) glutaraldehyde solution per 1 ml GOx-HSA mixture. This embodiment may yield a protein pellet that can remain physically and chemically stable for more than one year.

In another embodiment, the same procedure described above and illustrated in FIG. 2 may be utilized employing a GOx concentration of approximately 150,000 U/ml with an HSA concentration of approximately 32.5% (w/v). In such an embodiment, the GOx-HSA mixture may be immobilized with approximately 100 µl of a 12.5% (w/w) glutaraldehyde solution per 1 ml GOx-HSA mixture.

Those skilled in the art will of course understand that the concentrations of GOx, HSA, and glutaraldehyde incorporated in these embodiments could be varied without diverting from the scope or spirit of the invention.

Another embodiment of the invention involves further enhancing the operational activity of the protein matrix by utilizing additives in the protein mixture. For example, one embodiment involves adding another substance, such as a volume of silicone particles, to the protein mixture to possibly enhance operational stability. The addition of the silicone particles to a protein mixture may result in the sensing device maintaining its sensitivity for a longer time. It is believed that the silicone particles prevents oxygen depletion significant enough to increase the rate of product specific enzyme deactivation. The example embodiment illustrated in FIG. 2 and described above remains the same in this embodiment, with the only difference being the addition of another substance, such as silicone particles, to the protein mixture. In the embodiment utilizing silicone particles, the silicone particles added may be approximately 1% (w/v) to 5% (w/v) by volume so as to not change the response of a sensor in which the resultant protein pellet could ultimately be utilized. However, in other embodiments, either more or less silicone could be added to the protein mixture. In this embodiment, the total volume of the silicone particles added is preferably less than 20% of the volume of the SMP pellet. Those skilled in the art will understand that the volume of silicone added and the precise size of the silicone particles can be varied through experimentation without straying from the scope or spirit of the invention.

FIGS. 8a and 8b show glucose calibration curves for sensors employing protein matrices with no additive (8a) and with a silicone additive (8b). The tightness of the calibration bands indicates the stability of the sensor. When a sensor loses its activity, then the calibration curve may tend to drift, as illustrated in FIG. 8a. The drift is not as pronounced in FIG. 8b when the protein matrix includes a silicone additive.

The embodiments described above can be utilized to prepare any protein matrix. It has been found a protein matrix formulated by the above embodiments may be particularly well suited for use in both short term and long term biosensors. The immobilization process can produce a protein matrix that is physically and chemically stable over time. The final protein matrix can be formed with the advantageous qualities of being low swelling, non-leaching, and having high activity and high mechanical strength properties. These properties are essential to the creation of long lived and stable sensors.

Although the embodiments described above were described, by way of example, with reference to formulating and immobilizing glucose oxidase, other embodiments may formulate proteins and/or enzymes other than glucose oxidase. For example, in other embodiments, proteins and/or enzymes such as hexose oxidase, lactose oxidase, and the like, could also be formulated and immobilized. Those skilled in the art will appreciate and understand that the process is applicable to a wide variety of protein and/or enzymes.

In addition, while the embodiments described above are described, by way of example, in terms of forming or molding a protein pellet that may be used in a sensing device, those skilled in the art will appreciate and understand that embodiments of the process could be utilized to form or mold biological tissue replacements, arteries, heart valves, and the like. This may be done, for example, by immobilizing blood plasma proteins in a mold shaped as an artery, heart valve, and the like. The immobilization process should yield an artificial artery, heart valve, and the like, that is mechanically and chemically stable.

The embodiments disclosed herein are to be considered in all respects as illustrative and not restrictive of the invention. The scope of the invention is indicated by the appended claims, rather than the foregoing description. All changes that come within the meaning and range of equivalency of the claims are therefore intended to be embraced therein.

What is claimed is:

1. A molded protein material for a sensor comprising:
a protein component comprising at least one protein, the protein component being combined with a cross-linking reagent, wherein said molded protein material is in the form of a pellet.

2. The molded protein material of claim 1, comprising a protein component that has been exposed to a vapor phase cross-linking process.

3. The molded protein material of claim 2, comprising a protein component that has been incubated prior to the protein component having been exposed to the vapor phase cross-linking process.

4. The molded protein material of claim 2, comprising a protein component which has been immersed in a cross-linking solution after exposure to the vapor phase cross-linking process.

5. The molded protein material of claim 1, comprising a protein component that has been exposed to a vapor phase that is approximately 12.5% (w/w) glutaraldehyde for approximately 16 hours.

6. The molded protein material of claim 2, comprising a protein component that has been maintained at approximately room temperature for approximately two hours prior to exposure to the vapor phase cross-linking process.

7. The molded protein material of claim 2, comprising a protein component that has been immersed in a cross-linking solution by submerging in a buffered solution that is approximately 2.5% (w/w) glutaraldehyde for approximately one hour, after exposure to the vapor phase cross-linking process.

8. The molded protein material of claim 1, wherein the protein component comprises glucose oxidase and human serum albumin.

9. The molded protein material of claim 1, wherein the cross-linking reagent comprises glutaraldehyde.

10. The molded protein material of claim 8, wherein the cross-linking reagent comprises glutaraldehyde.

11. The molded protein material of claim 1, wherein the cross-linking reagent is selected from a group consisting of glutaraldehyde, disuccinimidyl suberate (DSS), and 1-Ethyl-3 (3-Dimethylaminopropyl) Carbodiimide (EDC).

12. The molded protein material the claim 8, wherein the glucose oxidase has a concentration that is between about 67,000 U/ml and about 150,000 U/ml.

13. The molded protein material of claim 12, wherein the human serum albumin has a concentration that is between about 23% (w/v) and about 32.5% (w/v) of the combined protein component and cross-linking agent.

14. The molded protein material of claim 1, wherein said pellet is semi-cylindrical shaped.

15. The molded protein material according to claim 1, wherein the protein component further comprises silicone particles.

16. The molded protein material of claim 15, wherein the protein comprises less than about 20% silicon particles by volume.

17. The molded protein material of claim 1, wherein the protein material is molded into a pellet sized to be a line-to-line fit for a sensor housing.

18. The molded protein material of claim 1, wherein the protein material is molded into a pellet slightly oversized with respect to a sensor housing so as to fit snugly therein.

19. The molded protein material of claim 1, wherein the shape of the protein material is determined by molding, followed by cutting the molded protein material.

20. The molded protein material of claim 1, wherein said protein material is in the form of a pellet having a rectangular cross-section.

21. The molded protein material of claim 1, wherein said protein material is in the form of a pellet having a semi-circular cross-section.

22. The molded protein of claim 1, wherein the pellet has a three-dimensional shape corresponding to three dimensions of a shape of a mold in which the pellet was formed.

23. A molded protein material for disposing in a sensor, said molded protein material formed into a pellet by hardening the same inside and according to dimensions of a mold, and comprising of glucose oxidase, human serum albumin, and a cross-linking reagent.

24. The protein material as recited in claim 23, wherein the protein material is solidified into a pellet before disposing in the sensor.

25. The molded protein material as recited in claim 23, wherein the pellet has a three-dimensional shape corresponding to three dimensions of a shape of the mold in which the pellet was formed.

26. A molded protein material for a sensor comprising:
 a protein component comprising at least one protein, the protein component being
 combined with a cross-linking reagent, wherein said molded protein material is in the form of a pellet
 wherein the protein component comprises glucose oxidase and human serum albumin;
 wherein the human serum albumin has a concentration that is between approximately 23% (w/v) and 32.5% (w/v) of the combined protein component and cross-linking agent.

* * * * *